United States Patent
Li et al.

(10) Patent No.: US 9,351,700 B2
(45) Date of Patent: May 31, 2016

(54) SCANNING METHOD AND DEVICE WITH REDUCED SCANNING DOSAGE

(71) Applicant: Shenyang Neusoft Medical Systems Co., Ltd., Shenyang (CN)

(72) Inventors: Xinliang Li, Shenyang (CN); Ling Pang, Shenyang (CN); Shanshan Lou, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 198 days.

(21) Appl. No.: 14/142,951

(22) Filed: Dec. 30, 2013

(65) Prior Publication Data

US 2015/0085984 A1  Mar. 26, 2015

(30) Foreign Application Priority Data

Sep. 26, 2013  (CN) .......................... 2013 1 0444867

(51) Int. Cl.
| | | |
|---|---|---|
| A61B 6/03 | (2006.01) | |
| H05G 1/32 | (2006.01) | |
| H05G 1/40 | (2006.01) | |
| A61B 6/00 | (2006.01) | |
| H05G 1/38 | (2006.01) | |
| H05G 1/46 | (2006.01) | |

(52) U.S. Cl.
CPC ................ *A61B 6/583* (2013.01); *A61B 6/405* (2013.01); *A61B 6/541* (2013.01); *A61B 6/542* (2013.01); *H05G 1/32* (2013.01); *H05G 1/40* (2013.01); *A61B 6/032* (2013.01); *A61B 6/482* (2013.01); *A61B 6/486* (2013.01); *A61B 6/503* (2013.01); *A61B 6/5258* (2013.01); *A61B 6/545* (2013.01); *H05G 1/38* (2013.01); *H05G 1/46* (2013.01)

(58) Field of Classification Search
CPC .............. A61B 6/00; A61B 6/03; A61B 6/40; A61B 6/405; A61B 6/48; A61B 6/482; A61B 6/486; A61B 6/50; A61B 6/503; A61B 6/54; A61B 6/541; A61B 6/542; A61B 6/545; A61B 6/58; A61B 6/582; A61B 6/583; H05G 1/00; H05G 1/08; H05G 1/26; H05G 1/30; H05G 1/32; H05G 1/38; H05G 1/40; H05G 1/46; H05G 1/62
USPC ............. 378/4–20, 91, 95–97, 101, 108, 114, 378/115, 117, 204, 207, 210, 901
See application file for complete search history.

(56) References Cited

U.S. PATENT DOCUMENTS

| | | | |
|---|---|---|---|
| 5,379,333 A | 1/1995 | Toth | |
| 5,400,378 A | 3/1995 | Toth | |
| 5,450,462 A | 9/1995 | Toth et al. | |
| 6,560,309 B1* | 5/2003 | Becker | .................... A61B 6/541 378/8 |
| 2006/0188058 A1* | 8/2006 | Bruder | .................... A61B 6/503 378/8 |
| 2007/0027389 A1* | 2/2007 | Wesse | .................... A61B 6/032 600/407 |
| 2008/0232542 A1 | 9/2008 | Lin | |
| 2012/0014499 A1* | 1/2012 | Feuerlein | ................ A61B 6/032 378/5 |

FOREIGN PATENT DOCUMENTS

| | | |
|---|---|---|
| CN | 1615797 A | 5/2005 |
| CN | 1942141 A | 4/2007 |
| CN | 102100562 A | 6/2011 |

\* cited by examiner

*Primary Examiner* — Anastasia Midkiff
(74) *Attorney, Agent, or Firm* — Kilpatrick Townsend & Stockton LLP

(57) ABSTRACT

A scanning method and device are provided. The method includes: determining values for a first scanning dosage and a second scanning dosage used in a scanning process based on a trigger condition which varies regularly and attenuation fluctuations of an object to be scanned, wherein the first scanning dosage is higher than the second scanning dosage, and at least one of the first scanning dosage and the second scanning dosage has an inconstant value; and scanning a target position with the determined values. In the present disclosure, a scanning dosage may be reduced and different image noises may be kept consistent.

18 Claims, 7 Drawing Sheets

SCANNING METHOD AND DEVICE WITH REDUCED SCANNING DOSAGE

CROSS-REFERENCE TO RELATED APPLICATIONS

The present application on claims priority to Chinese patent application No. 201310444867.1, filed on Sep. 26, 2013, and entitled "SCANNING METHOD AND DEVICE WITH REDUCED SCANNING DOSAGE", and the entire disclosure of which is incorporated herein by reference.

FIELD OF THE DISCLOSURE

The present disclosure generally relates to medical diagnosis devices, and more particularly, to a scanning method and device with a reduced scanning dosage.

BACKGROUND OF THE DISCLOSURE

To protect patient organs, in some CT scanning, total scanning dosage values need to be controlled as low as possible. In clinical practices, a factor which varies regularly in a certain stage is generally taken as a trigger condition for realizing a periodical control of the scanning dosage, that is, scanning is performed under an alternation between a scanning mode of low scanning dosage and a scanning mode of high scanning dosage. For example, referring to FIG. 1, during a heart scanning, according to electrocardio signal fluctuations of a patient, a predetermined constant high scanning dosage is used in the scanning during a first time period while a predetermined constant low scanning dosage is used in the scanning during a second time period. For another example, to protect thyroids or eyes during a scanning process, when a radiation tube is facing directly to the thyroids or the eyes, a predetermined constant low scanning dosage should be used in the scanning; and when the radiation tube deflects from the direction straightly towards the thyroids or the eyes, a predetermined constant high scanning dosage is used in the scanning.

However, the inventors found at least following disadvantages in conventional technologies. As described above, a conventional scanning process is performed under an alternation between a scanning mode with low scanning dosage and a scanning mode with high scanning dosage, where a factor which varies regularly is taken as a trigger condition. In the above described conventional process, the total scanning dosage in the scanning is reduced and thus a scanned organ is protected in a manner. However, when scanning different parts of a body or scanning a same part from different scanning angles, attenuation of X-rays is different. Therefore, when a constant high scanning dosage or a constant low scanning dosage is used in scanning, image noises generated from scanning different parts of the body may be inconsistent, and image noises generated from scanning a same part of the body with different scanning angles may be inconsistent as well.

SUMMARY

Embodiments of the present disclosure provide a scanning method and device, where a scanning dosage may be reduced and different image noises may be consistent.

In an embodiment, a scanning method may be provided, including:

determining values for a first scanning dosage and a second scanning dosage used in a scanning process based on a trigger condition which varies regularly and attenuation fluctuations of an object to be scanned, wherein the first scanning dosage is higher than the second scanning dosage, and at least one of the first scanning dosage and the second scanning dosage has an inconstant value; and scanning a target position with the inconstant scanning dosage.

Optionally, when the first scanning dosage has an inconstant value, the second scanning dosage has a constant value which is determined according to the trigger condition which varies regularly.

Optionally, the second scanning dosage is zero.

Optionally, when the second scanning dosage has an inconstant value, first scanning dosage has a constant value which is determined according to the trigger condition which varies regularly.

Optionally, when the second scanning dosage has an inconstant value, the step of determining values for a first scanning dosage and a second scanning dosage used in a scanning process based on a trigger condition which varies regularly and attenuation fluctuations of an object to be scanned may include: determining to use the inconstant second scanning dosage to scan the target position according to the trigger condition which varies regularly; and adjusting the second scanning dosage to be a dosage which varies with the target position or varies with the target position and a scanning angle based on a dosage adjustment mode to ensure image noise congruence Optionally, when the first scanning dosage has an inconstant value, the step of determining values for a first scanning dosage and a second scanning dosage used in a scanning process based on a trigger condition which varies regularly and attenuation fluctuations of an object to be scanned may include: determining to use the inconstant first scanning dosage to scan the target position according to the trigger condition which varies regularly; and adjusting the first scanning dosage to be a dosage which varies with the target position or varies with the target position and a scanning angle based on a dosage adjustment mode to ensure image noise congruence.

Optionally, the step of adjusting the second scanning dosage to be a dosage which varies with the target position or varies with the target position and a scanning angle based on a dosage adjustment mode to ensure image noise congruence may include:

calculating a first set of dosage values for the second scanning dosage based on equation $$N_j = DoseRightFactor \times N_{low} \times \left( \frac{e^{(-\mu_{water} * D_{ref})}}{e^{(-\mu_{water} * D_j)}} \right)^{adjCoef},$$

wherein the first set of dosage values are used for scanning different target positions; and calculating a second set of dosage values for the second scanning dosage based on equation $$N_i = \frac{N_j}{\sum_{i=1}^{V} \sqrt{A_{max,i}}} * \sqrt{A_{max,i}},$$

wherein the second set of dosage values are used for scanning one target position from different scanning angles, wherein $N_j$ is a scanning dosage on a $j^{th}$ target position, DoseRightFactor is an image noise coefficient, $N_{low}$ is the second scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

Optionally, the step of adjusting the first scanning dosage to be a dosage which varies with the target position or varies with the target position and a scanning angle based on a dosage adjustment mode to ensure image noise congruence may include:

calculating a first set of dosage values for the first scanning dosage based on equation $$N_j = DoseRightFactor \times N_{high} \times \left( \frac{e^{(-\mu_{water}*D_{ref})}}{e^{(-\mu_{water}*D_j)}} \right)^{adjCoef},$$

wherein the first set of dosage values are used for scanning different target positions; and calculating a second set of dosage values for the first scanning dosage based on equation $$N_i = \frac{N_j}{\sum_{i=1}^{V} \sqrt{A_{max,i}}} * \sqrt{A_{max,i}},$$

wherein the second set of dosage values are used for scanning one target position from different scanning angles, wherein $N_j$ is a scanning dosage on a $j^{th}$ target position, DoseRightFactor is an image noise coefficient, $N_{high}$ is the first scanning dosage, $\mu_{water}$ is an attenuation coefficient of water, $D_{ref}$ is a referenced equivalent diameter of the water phantom, $D_j$ is an equivalent diameter of the water phantom on the $j^{th}$ filet target position, adjCoef is an exponent adjustment parameter of a current in a tube filament, $N_i$ is a scanning dosage of a $i^{th}$ scanning angle on $j^{th}$ target position, $A_{max,i}$ is maximum attenuation of all channels of the $i^{th}$ scanning angle, and V is the total number of scanning angles in a round of scanning.

Optionally, when the target position is being scanned with the determined values, a current in a tube filament is under open-loop control.

Optionally, the method may further include: during a transition process from a first scanning dosage stage to a second scanning dosage stage, implementing real-time calculation to obtain a time period for transmission from a current scanning dosage to an initial scanning dosage in a third scanning dosage stage performed after the second scanning dosage stage; implementing real-time comparison between the calculated time period and a preset time period; and if the calculated time period is longer than or equal to the preset time period, terminating the transition process from the first scanning dosage stage to the second scanning dosage stage, terminating the second scanning dosage stage, and transiting to the third scanning dosage stage from a current time point.

Optionally, the initial scanning dosage in the third scanning dosage stage may be predicted by following steps: fitting an equivalent diameter of the water phantom on a target position where the initial scanning dosage is used based on equivalent diameters of the water phantom of a plurality of parts obtained in previous scannings; calculating a ratio of the equivalent diameter of water phantom on the target position where the initial scanning dosage is used to an equivalent diameter of the water phantom on a target position where the current scanning dosage is used; and calculating a product of the ratio and the current scanning dosage as the initial scanning dosage in the third scanning dosage stage.

In an embodiment, a scanning device may be provided, including:

a scanning dosage determination unit, adapted to determine values for a first scanning dosage and a second scanning dosage used in a scanning process based on a trigger condition which varies regularly and attenuation fluctuations of an object to be scanned, wherein the first scanning dosage is higher than the second scanning dosage, and at least one of the first scanning dosage and the second scanning dosage has an inconstant value; and a scanning unit, adapted to scan a target position with the determined values.

Optionally, when the first scanning dosage has an inconstant value, the second scanning dosage has a constant value which is determined according to the trigger condition which varies regularly.

Optionally, the second scanning dosage is zero.

Optionally, when the second scanning dosage has an inconstant value, the first scanning dosage has a constant value which is determined according to the trigger condition which varies regularly.

Optionally, when the second scanning dosage has an inconstant value, the scanning dosage determination unit may include:

a first scanning mode determination sub-unit, adapted to determine to use the inconstant second scanning dosage to scan the target position according to the trigger condition which varies regularly; and a first scanning dosage adjustment sub-unit, adapted to adjust the second scanning dosage to be a dosage which varies with the target position or varies with the target position and a scanning angle based on a dosage adjustment mode to ensure image noise congruence.

Optionally, when the first scanning dosage has an inconstant value, the scanning dosage determination unit may include:

a second scanning mode determination sub-unit, adapted to determine to use the inconstant first scanning dosage to scan the target position according to the trigger condition which varies regularly; and a second scanning dosage adjustment sub-unit, adapted to adjust the first scanning dosage to be a dosage which varies with the target position or varies with the target position and a scanning angle based on a dosage adjustment mode to ensure image noise congruence.

Optionally, the first scanning dosage adjustment sub-unit may include:

a first position scanning dosage calculation sub-unit, adapted to calculate a first set of dosage values for the second scanning dosage based on equation $$N_j = DoseRightFactor \times N_{low} \times \left( \frac{e^{(-\mu_{water}*D_{ref})}}{e^{(-\mu_{water}*D_j)}} \right)^{adjCoef},$$

wherein the first set of dosage values are used for scanning different target positions; and a first angle scanning dosage calculation sub-unit, adapted to calculate a second set of dosage values for the second scanning dosage based on equation $$N_i = \frac{N_j}{\sum_{i=1}^{V} \sqrt{A_{max,i}}} * \sqrt{A_{max,i}},$$

wherein the second set of dosage values are used for scanning one target position from different scanning angles, wherein $N_j$ is a scanning dosage on a $j^{th}$ target position, DoseRightFactor is an image noise coefficient, $N_{low}$ is the second scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

Optionally, the second scanning dosage adjusting sub-unit may include:

a second position scanning dosage calculation sub-unit, adapted to calculate a first set of dosage values for the first scanning dosage based on equation $$N_j = DoseRightFactor \times N_{high} \times \left( \frac{e^{(-\mu_{water}*D_{ref})}}{e^{(-\mu_{water}*D_j)}} \right)^{adjCoef},$$

wherein the first set of dosage values are used for scanning different target positions; and a second angle scanning dosage calculation sub-unit, adapted to calculate a second set of dosage values for the first scanning dosage based on equation $$N_i = \frac{N_j}{\sum_{i=1}^{V} \sqrt{A_{max,i}}} * \sqrt{A_{max,i}},$$

wherein the second set of dosage values are used for scanning one target position from different scanning angles, wherein $N_j$ is a scanning dosage on a $j^{th}$ target position, DoseRightFactor is an image noise coefficient, $N_{high}$ is the first scanning dosage, $\mu_{water}$ is an attenuation coefficient of water, $D_{ref}$ is a referenced equivalent diameter of the water phantom, $D_j$ is an equivalent diameter of the water phantom on filet target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

Optionally, when the scanning unit scans the target position with the determined values, a current in a tube filament is under open-loop control.

Optionally, the device may further include:

a real-time calculation unit, adapted to implement real-time calculation to obtain a time period for transmission from a current scanning dosage to an initial scanning dosage in a third scanning dosage stage performed after the second scanning dosage stage, during a transition process from a first scanning dosage stage to a second scanning dosage stage;

a real-time comparison unit, adapted to implement real-time comparison between the calculated time period and a preset time period; and a transition unit, adapted to terminate the transition process from the first scanning dosage stage to the second scanning dosage stage, terminate the second scanning dosage stage, and transit to the third scanning dosage stage from a current time point, if the calculated time period is longer than or equal to the preset time period.

Optionally, the real-time calculation unit may include:

a fitting sub-unit, adapted to fit an equivalent diameter of the water phantom on a target position where the initial scanning dosage is used based on equivalent diameters of the water phantom of a plurality of parts obtained in previous scannings;

a ratio calculation sub-unit, adapted to calculate a ratio of the equivalent diameter of water phantom on the target position where the initial scanning dosage is used to an equivalent diameter of the water phantom on a target position where the current scanning dosage is used; and an initial scanning dosage calculation sub-unit, adapted to calculate a product of the ratio and the current scanning dosage as the initial scanning dosage in the third scanning dosage stage.

Compared with the conventional solutions, the present disclosure may have following advantages.

In the present disclosure, a constant scanning dosage is adjusted to an inconstant scanning dosage by a dosage adjusting method and the inconstant scanning dosage is used in scanning. The inconstant scanning dosage (including a first inconstant scanning dosage and a second inconstant scanning dosage) varies with a target position and a scanning angle, so that the scanning dosage may have a relatively low value and image noise congruence may be ensured.

BRIEF DESCRIPTION OF THE DRAWINGS

In order to clarify the disclosure and advantages of the present disclosure, accompanying drawings used in description of embodiments of the present disclosure will be described simply. Obviously, drawings described below are only illustrative and those skilled in the art can obtain other drawings based on these drawings without creative works.

DETAILED DESCRIPTION OF THE DISCLOSURE

During a CT scanning, to a same part, the greater the scanning dosage is, the less the noise generated in image reconstruction may be. When scanning different parts of a body or scanning a same part from different scanning angles, attenuation of X-rays is different. Therefore, when a constant high scanning dosage or a constant low scanning dosage is used in scanning, image noises generated from scanning different parts of the body may be inconsistent, and image noises generated from scanning a same part of the body with different scanning angles may be inconsistent as well. Therefore, various dosage adjusting modes are used in CT scanning in clinical practices, so as to ensure that image noises generated from scanning different parts of a patient or from scanning the same part with different scanning angles are consistent. Since scanning different parts of a body or scanning a same part from different scanning angles results in different attenuation levels to X-rays, the dosage adjusting means using different scanning dosages to scan different parts of a patient or to scan a same part with different scanning angles, which ensures image noises generated are consistent.

A scanning method and device with a reduced scanning dosage are provided in embodiments of the present disclosure. In the present disclosure, a constant scanning dosage is adjusted to be an inconstant scanning dosage by using a dosage adjusting method, and the adjusted inconstant scanning dosage is used in scanning, The inconstant scanning dosage varies with a target position and a scanning angle, so that the scanning dosage may have a relatively low value and image noise congruence may be ensured. It should be noted that, values of a scanning dosage used in a scanning process in embodiments of the present disclosure may include a first scanning dosage and a second scanning dosage. Hereinafter, the first scanning dosage may be called a high scanning dosage and the second scanning dosage may be called a low scanning dosage.

Particularly, a new dosage adjusting method is provided to change a constant scanning dosage into an inconstant scanning dosage.

In order to clarify the objects, characteristics and advantages of the disclosure, embodiments of present disclosure will be described in detail in conjunction with accompanying drawings.

Figure 1:
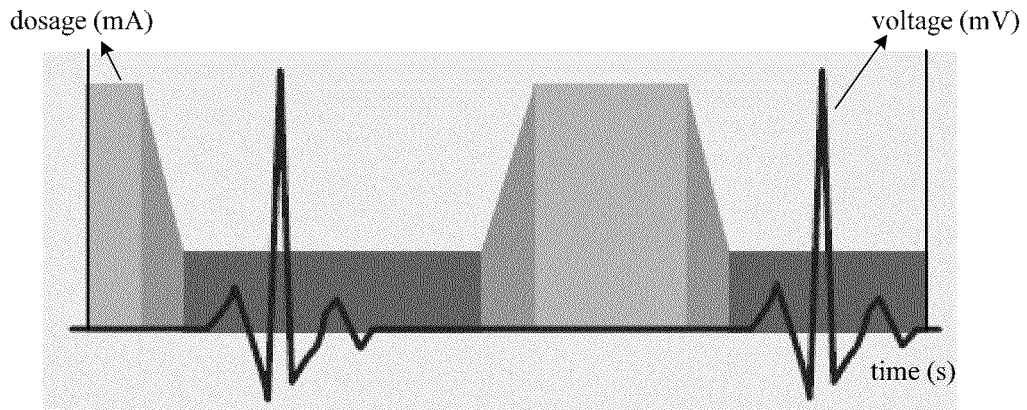
FIG. 1 schematically illustrates scanning using a high scanning dosage or a low scanning dosage based on variations of electrocardio signals in existing techniques.
Figure 2:
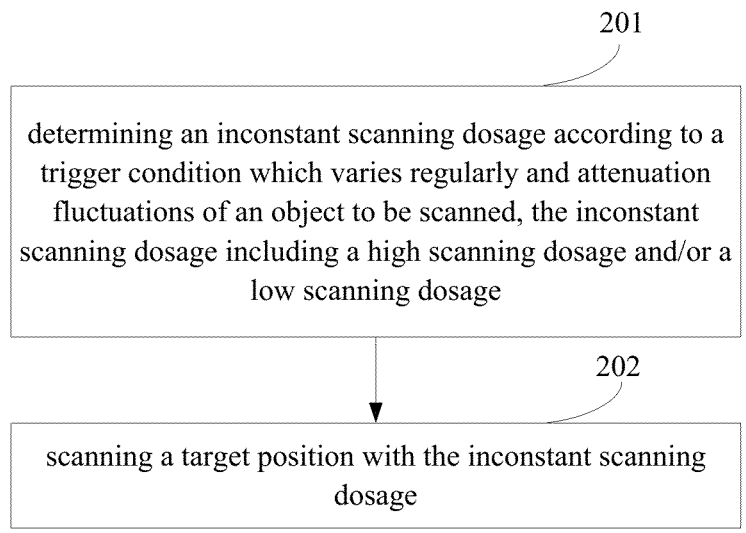
FIG. 2 schematically illustrates a flow chart of a scanning method according to one embodiment of the present disclosure.

FIG. 2 schematically illustrates a flow chart of a scanning method according to one embodiment of the present disclosure. The scanning method may include following steps 201 and 202.

In 201, determining an inconstant scanning dosage according to a trigger condition which varies regularly and attenuation fluctuations of an object to be scanned, the inconstant scanning dosage including a high scanning dosage and/or a low scanning dosage.

In existing techniques, a factor which varies regularly in a certain stage is generally taken as a trigger condition for determining a constant scanning dosage, that is, scanning with a constant low scanning dosage or with a constant high scanning dosage. For example, when scanning a heart, a change of electrocardio signals of a patient is taken as the trigger condition. For another example, a change of a scanning angle is taken as the trigger condition.

In some embodiments, "a factor which varies regularly" may be any trigger conditions in existing techniques and is not limited here.

"An inconstant scanning dosage" may be a scanning dosage varying with a target position, or a scanning dosage varying with a target position and a scanning angle.

In some embodiments, when the inconstant scanning dosage is a high scanning dosage, the low scanning dosage is a constant value which is determined according to the trigger condition which varies regularly. In some embodiments, the low scanning dosage is zero.

In some embodiments, determining an inconstant low scanning dosage according to a trigger condition which varies regularly and attenuation fluctuations of an object to the scanned may include: determining the scanning dosage on the target position to be a constant low scanning dosage according to the trigger condition which varies regularly; and adjusting the constant low scanning dosage to a low scanning dosage which varies with the target position or varies with the target position and a scanning angle according to a dosage adjustment mode of image noise congruence.

In some embodiments, when the inconstant scanning dosage is a low scanning dosage, the high scanning dosage is a constant value which is determined according to the trigger condition which varies regularly.

In some embodiments, determining an inconstant high scanning dosage according to a trigger condition which varies regularly and attenuation fluctuations of an object to be scanned may include: determining the scanning dosage on the target position to be a constant high scanning dosage according to the trigger condition which varies regularly; and adjusting the constant high scanning dosage to a high scanning dosage which varies with the target position or varies with the target position and a scanning angle according to a dosage adjustment mode of image noise congruence.

In S202, scanning a target position with the inconstant scanning dosage.

Compared with the conventional solutions, embodiments of the present disclosure have following advantages. An inconstant scanning dosage is determined according to two factors, including a trigger condition which varies regularly and attenuation fluctuations of an object to be scanned. The inconstant scanning dosage (including an inconstant high scanning dosage and an inconstant low scanning dosage) varies with a target position or a scanning angle on a same target position, so that the scanning dosage may have a relatively low value and image noise congruence may be ensured.

It should be noted that, there are various dosage adjusting methods for ensuring image noise congruence in conventional solutions. In embodiments of the present disclosure any conventional dosage adjusting method may be employed to change a constant scanning dosage (including a constant low scanning dosage and/or a constant high scanning dosage) to an inconstant scanning dosage (including an inconstant low scanning dosage and/or an inconstant high scanning dosage).

In some embodiments, a following dosage adjusting method may be employed to adjust a low scanning dosage (the low scanning dosage varying with the target position and the scanning angle).

First, calculating low scanning dosages on different target positions based on equation $$N_j = DoseRightFactor \times N_{low} \times \left( \frac{e^{(-\mu_{water} * D_{ref})}}{e^{(-\mu_{water} * D_j)}} \right)^{adjCoef},$$

where if the low scanning dosages only vary with the target positions, the inconstant low scanning dosage may be obtained based on this equation.

Afterward, calculating low scanning dosages used for scanning one target position from different scanning angles based on equation $$N_i = \frac{N_j}{\sum_{i=1}^{V} \sqrt{A_{max,i}}} * \sqrt{A_{max,i}},$$

where $N_j$ is a scanning dosage on a $j^{th}$ target position, DoseRightFactor is an image noise coefficient, $N_{low}$ is the constant low scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

Last, performing scanning based on the calculated low scanning dosages on different target positions and the calculated low scanning dosages used for scanning one target position from different scanning angles.

In some embodiments, a following dosage adjusting method may be employed to adjust a high scanning dosage which varies with the target position and the scanning angle.

First, calculating high scanning dosages on different target positions based on equation $$N_j = DoseRightFactor \times N_{high} \times \left( \frac{e^{(-\mu_{water} * D_{ref})}}{e^{(-\mu_{water} * D_j)}} \right)^{adjCoef},$$

where if the high scanning dosages only vary with the target positions, the inconstant high scanning dosage may be obtained based on this equation.

Afterward, calculating high scanning dosages used for scanning one target position from different scanning angles based on equation $$N_i = \frac{N_j}{\sum_{i=1}^{V} \sqrt{A_{max,i}}} * \sqrt{A_{max,i}},$$

where $N_j$ is a scanning dosage on a $j^{th}$ target position, DoseRightFactor is an image noise coefficient, $N_{high}$ is the constant low scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

Last, performing scanning based on the calculated high scanning dosages on different target positions and the calculated high scanning dosages used for scanning one target position from different scanning angles.

In embodiments of the present disclosure, in one aspect, a low scanning dosage and/or a high scanning dosage have been changed into inconstant values. Therefore, when the low scanning dosage changes to the high scanning dosage, or, the high scanning dosage changes to the low scanning dosage, the change value may be great. In another aspect, a mode switch needs to be performed in a required time period in a CT system according to performance of the CT system, that is, a scanning dosage needs to be changed in the required time period in the CT system. However, when the scanning dosage is changed by a large margin, the CT system may not have the scanning dosage changed in the required time period.

It is found that, if a current in a tube filament is low, a changing rate of the scanning dosage may be slow, so that the scanning dosage may not be changed by a large margin in the required time period. That is to say, the change of the scanning dosage may not be completed in the required time period due to the changing rate thereof. Therefore, when the scanning dosage is changed by a large margin, to enable the scanning dosage to be changed in the required time period, the current in the tube filament may be under open-loop control other than a closed-loop control when the target position is being scanned with the scanning dosage. Under the open-loop control, a feedback adjusting process of the current in the filament may be avoided and the current in the tube filament is raised, thereby providing a faster changing rate of the scanning dosage.

Figure 3:
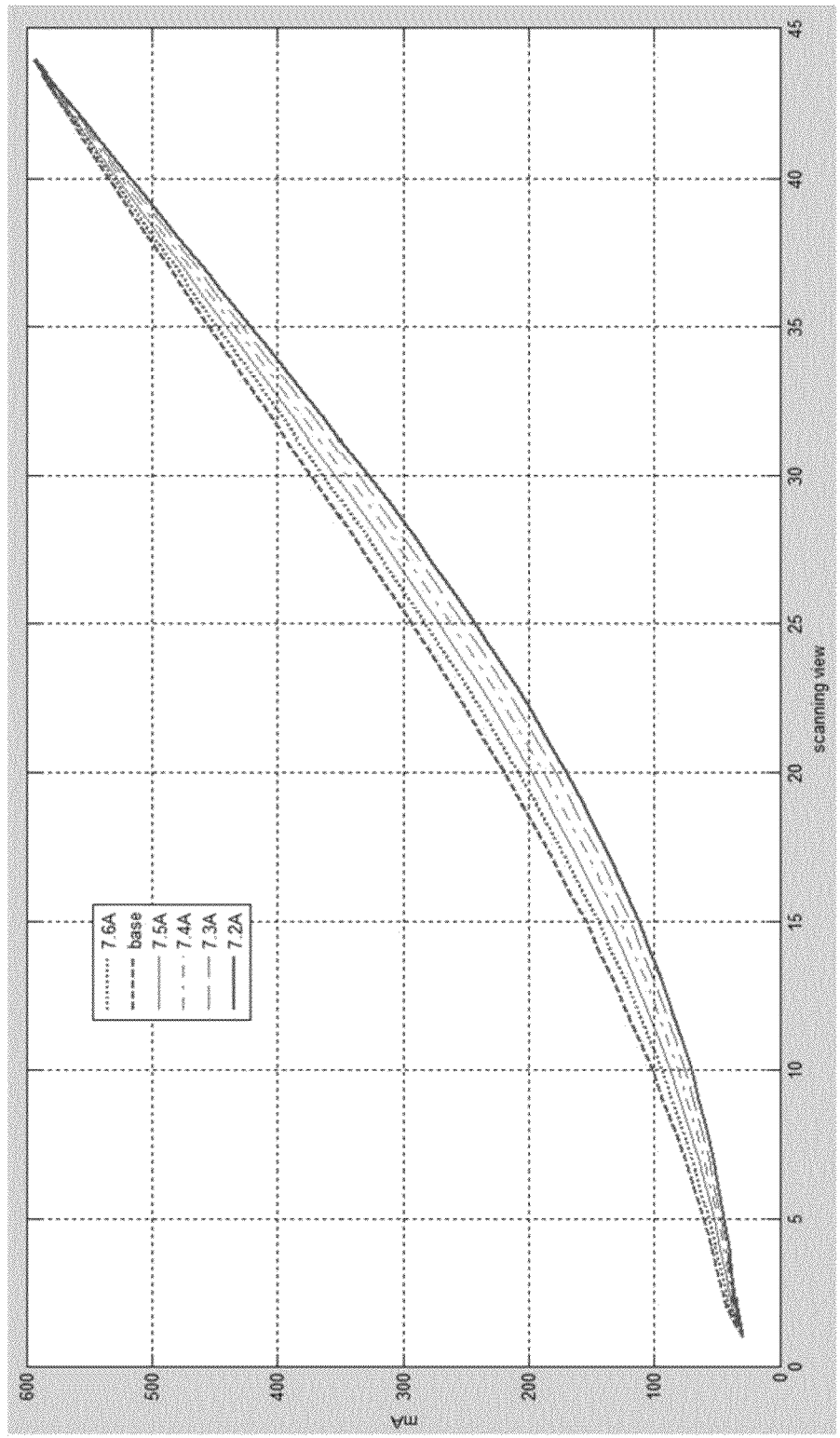
FIG. 3 schematically illustrates relationships between a changing rate of a scanning dosage and a current in a tube filament according to one embodiment of the present disclosure.

As shown in FIG. 3, from up to down, a back line crosses curves '7.6A', 'Base', '7.5A', '7.4A', '7.3A' and '7.2A' in turn. The higher the current in the filament, the faster the changing rate of the scanning dosage.

Except a mode for controlling the current in the filament is changed to be an open-loop control mode, or if the scanning dosage cannot be changed in a required time period by a large margin although an open-loop control mode is employed, a method for ensuring the scanning dosage to be changed in a required time period during a switch process may be provided. To ensure the scanning dosage to be changed by a large margin in the required time and further to ensure a next high scanning dosage stage not to be delayed, the method may include; during a transition process from a high scanning dosage stage to a low scanning dosage stage, once the low scanning dosage is changed, calculating a time period for transmission from a current scanning dosage to an initial high scanning dosage in a next high scanning dosage stage; and if the calculated time period is longer than or equal to the required time period, terminating the transition process from the high scanning dosage stage to the low scanning dosage stage and the low scanning dosage stage (the transition may not end at a current time point), and transiting to the next high scanning dosage immediately, so as to realize switching to the next high scanning dosage stage in the required time period.

Figure 4:
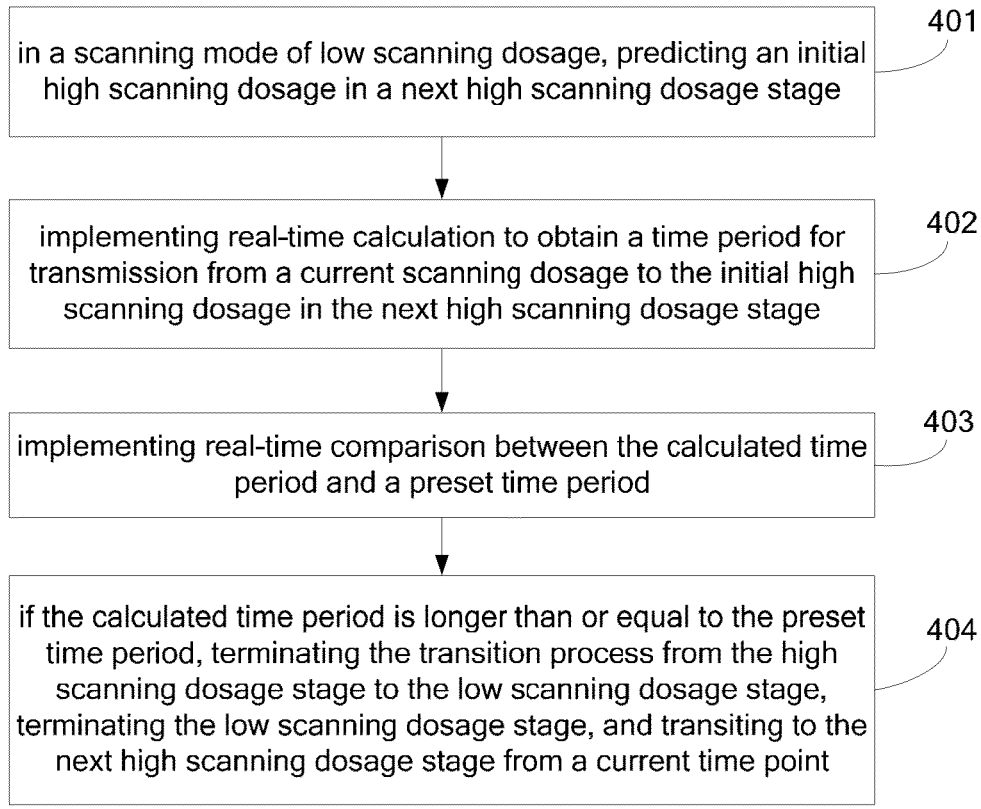
FIG. 4 schematically illustrates a flow chart of a method for transiting from a high scanning dosage stage to a low scanning dosage stage according to one embodiment of the present disclosure.

FIG. 4 schematically illustrates a flow chart of a method for transiting from a high scanning dosage stage to a low scanning dosage stage according to one embodiment of the present disclosure. The method includes following steps.

In 401, in a scanning mode of low scanning dosage, predicting an initial high scanning dosage in a next high scanning dosage stage.

In embodiments of the present disclosure, the low scanning dosage stage and the high scanning dosage stage disappear alternately. A low scanning dosage stage is followed by a high scanning dosage stage necessarily. Besides, in a high scanning dosage stage, the scanning dosage is inconstant and varies with target positions, or varies with target positions and scanning angles. Therefore, when transiting to the next high scanning dosage stage, a first high scanning dosage in the next high scanning dosage stage may be reached, i.e., the initial high scanning dosage. Therefore, the initial high scanning dosage in the next high scanning dosage stage may be predicted.

Figure 5:
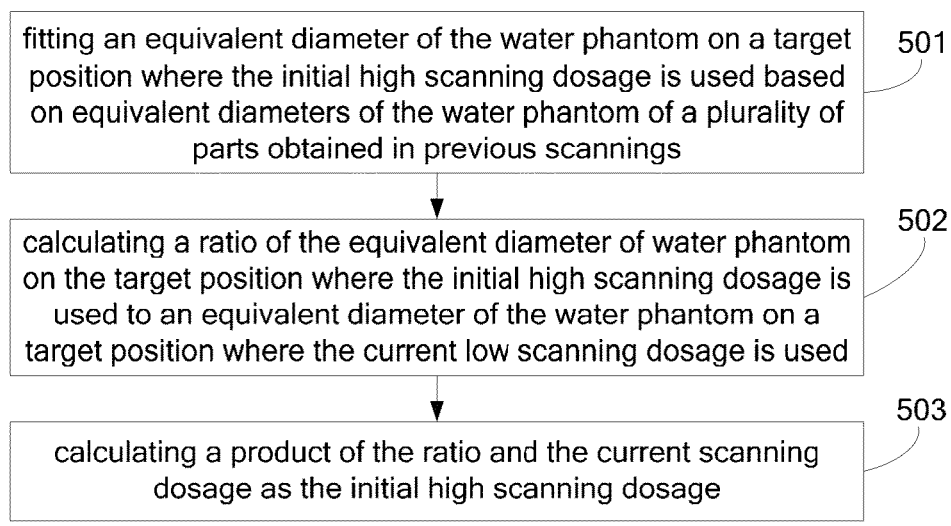
FIG. 5 schematically illustrates a flow chart of a method for predicting an initial high scanning dosage in a next high scanning dosage stage according to one embodiment of the present disclosure.

Referring to FIG. 5, the initial high scanning dosage in the next high scanning dosage stage may be predicted by following steps.

In 501, fitting an equivalent diameter of the water phantom on a target position where the initial high scanning dosage is used based on equivalent diameters of the water phantom of a plurality of parts obtained in previous scannings.

Before performing a formal scanning, a plurality of parts may be pre-scanned. The number of the plurality of pre-scanned parts is smaller than the number of target positions in the formal scanning. After obtaining equivalent diameters of the water phantom of the plurality of parts, the equivalent diameter of the water phantom on the target position where the initial high scanning dosage is used may be obtained by fitting. According to a trigger condition, a time point when the initial high scanning dosage is used may be determined. And the target position where the initial high scanning dosage is used may be further determined based on a scanning speed.

In 502, calculating a ratio of the equivalent diameter of water phantom on the target position where the initial high scanning dosage is used to an equivalent diameter of the water phantom on a target position where the current low scanning dosage is used.

In 503, calculating a product of the ratio and the current scanning dosage as the initial high scanning dosage.

The ratio of the equivalent diameter of water phantom on the target position where the initial high scanning dosage is used to the equivalent diameter of the water phantom on the target position where the current low scanning dosage is used may be equal to a ratio of the initial high scanning dosage to the current low scanning dosage. Therefore, after obtaining the ratio of the equivalent diameter of water phantom on the target position where the initial high scanning dosage is used to the equivalent diameter of the water phantom on the target position where the current low scanning dosage is used and the current low scanning dosage, the initial high scanning dosage may be obtained.

After the prediction process, the method may be back to the switch process and proceeding to following steps.

In 402, implementing real-time calculation to obtain a time period for transmission from a current scanning dosage to the initial high scanning dosage in the next high scanning dosage stage.

In 403, implementing real-time comparison between the calculated time period and a preset time period.

In 404, if the calculated time period is longer than or equal to the preset time period, terminating the transition process from the high scanning dosage stage to the low scanning dosage stage, terminating the low scanning dosage stage, and transiting to the next high scanning dosage stage from a current time point; or else, continuing the transition process from the high scanning dosage stage to the low scanning dosage stage.

It should be noted that, the above method may be adapted for transition from a low scanning dosage stage to a high scanning dosage stage. Similarly, to ensure the scanning dosage to be changed in the required time during a switch process and further to ensure a next low scanning dosage stage not to be delayed, the method may include: during a transition process from the low scanning dosage stage to the high scanning dosage stage, once the high scanning dosage is changed, calculating a time period for transmission from a current scanning dosage to an initial low scanning dosage in a next low scanning dosage stage; and if the calculated time period is longer than or equal to the required time period, terminating the transition process from the low scanning dosage stage to the high scanning dosage stage and the high scanning dosage stage (the transition may not end at a current time point), and transiting to the next low scanning dosage immediately, so as to realize switching to the next low scanning dosage stage in the required time period. FIGS. 4 and 5 illustrate detailed steps in the above process.

Compared with the conventional solutions, embodiments of the present disclosure have following advantages. An inconstant scanning dosage is determined according to two factors, including a trigger condition which varies regularly and attenuation fluctuations of an object to be scanned. The inconstant scanning dosage (including an inconstant high scanning dosage and an inconstant low scanning dosage) varies with a target position and a scanning angle on a same target position, so that the scanning dosage may have a relatively low value and image noise congruence may be ensured.

Further, a current high scanning dosage stage may be switched to a next high scanning dosage stage in a required time period, thereby avoiding delay of the next high scanning dosage stage.

Figure 6:
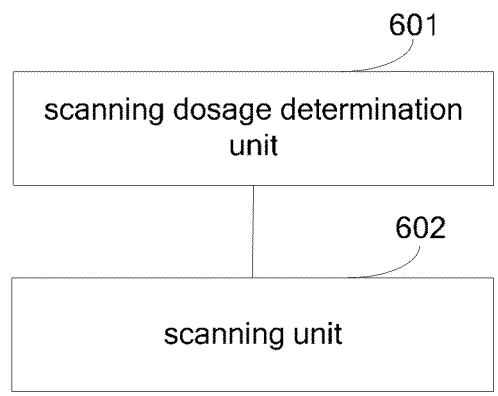
FIG. 6 schematically illustrates a block diagram of a scanning device according to one embodiment of the present disclosure.

Accordingly, in one embodiment, a scanning device is provided, FIG. 6 schematically illustrates a block diagram of a scanning device according to one embodiment of the present disclosure. The device includes a scanning dosage determination unit 601 and a scanning unit 602. Detailed structures in the device and connections of the structures may be described in conjunction with an operational principle of the device.

The scanning dosage determination unit 601 is adapted to determine an inconstant scanning dosage according to a trigger condition which varies regularly and attenuation fluctuations of an object to be scanned, the inconstant scanning dosage including a high scanning dosage and/or a low scanning dosage.

The scanning unit 602 is adapted to scan a target position with the inconstant scanning dosage.

In some embodiments, when the inconstant scanning dosage is a high scanning dosage, the low scanning dosage is a constant value which is determined according to the trigger condition which varies regularly. In some embodiments, the low scanning dosage is zero.

In some embodiments, when the inconstant scanning dosage is a low scanning dosage, the high scanning dosage is a constant value which is determined according to the trigger condition which varies regularly.

In some embodiments, when the inconstant scanning dosage is a low scanning dosage, the scanning dosage determination unit 601 may include: a low scanning mode determination sub-unit, adapted to determine the scanning dosage on the target position to be a constant low scanning dosage according to the trigger condition which varies regularly; and a low scanning dosage adjustment sub-unit, adapted to adjust the constant low scanning dosage to a low scanning dosage which varies with the target position or varies with the target position and a scanning angle according to a dosage adjusting mode of image noise congruence.

In some embodiments, when the inconstant scanning dosage is a high scanning dosage, the scanning dosage determination unit 601 may include: a high scanning mode determination sub-unit, adapted to determine the scanning dosage on the target position to be a constant high scanning dosage according to the trigger condition which varies regularly; and a high scanning dosage adjusting sub-unit, adapted to adjust the constant high scanning dosage to a high scanning dosage Which varies with the target position or varies with the target position and a scanning angle according to a dosage adjusting mode of image noise congruence.

Figure 7:
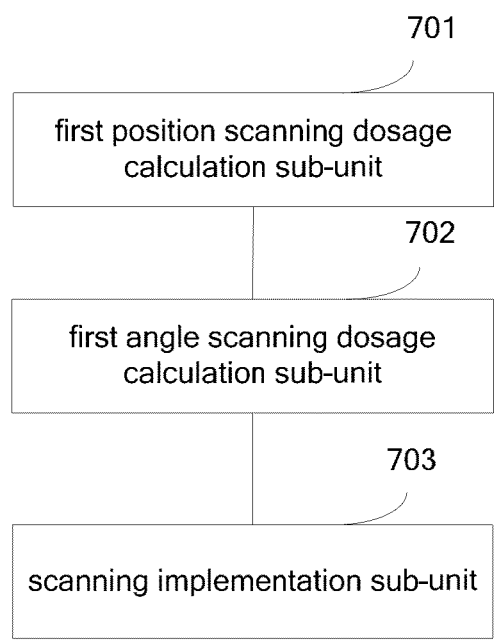
FIG. 7 schematically illustrates a block diagram of a low scanning dosage adjustment sub-unit according to one embodiment of the present disclosure.

In some embodiments, as shower in FIG. 7, the low sea dosage adjustment sub-unit includes a first position scanning dosage calculation sub-unit 701, a first angle scanning dosage calculation sub-unit 702 and a scanning implementation sub-unit 703.

The first position scanning dosage calculation sub-unit 701 is adapted to calculate low scanning dosages on different target positions based on equation $$N_j = DoseRightFactor \times N_{low} \times \left( \frac{e^{(-\mu_{water} \ast D_{ref})}}{e^{(-\mu_{water} \ast D_j)}} \right)^{adjCoef},$$

The first angle scanning dosage calculation sub-unit 702 is adapted to calculate low scanning dosages used for scanning one target position from different scanning angles based on equation $$N_i = \frac{N_j}{\sum_{i=1}^{V} \sqrt{A_{max,i}}} \ast \sqrt{A_{max,i}},$$

wherein $N_j$ is a scanning dosage on a $j^{th}$ target position, DoseRightFactor is an image noise coefficient, $N_{low}$ is the constant low scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

The scanning implementation sub-unit 703 is adapted to perform scanning based on the calculated scanning dosages on different target positions and the calculated scanning dosages used for scanning one target position from different scanning angles.

Figure 8:
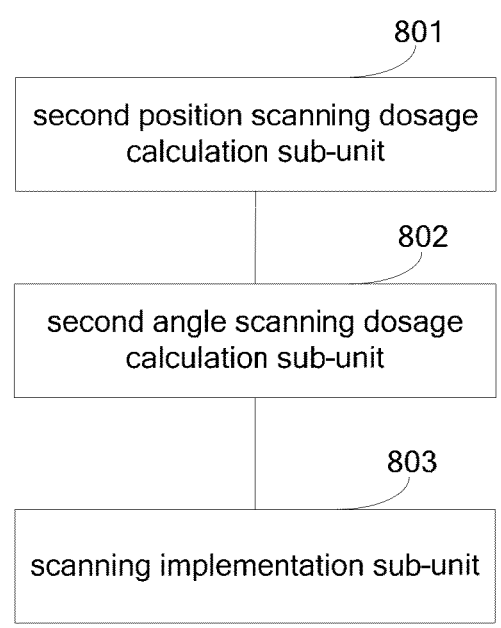
FIG. 8 schematically illustrates a block diagram of a high scanning dosage adjustment sub-unit according to one embodiment of the present disclosure.

In some embodiments, as shown in FIG. 8, the high scanning dosage adjustment sub-unit includes a second position scanning dosage calculation sub-unit 801, a second angle scanning dosage calculation sub-unit 802 and a scanning implementation sub-unit 803.

The second position scanning dosage calculation sub-unit 801 is adapted to calculate high scanning dosages on different target positions based on equation $$N_j = DoseRightFactor \times N_{high} \times \left( \frac{e^{(-\mu_{water} \ast D_{ref})}}{e^{(-\mu_{water} \ast D_j)}} \right)^{adjCoef},$$

The second angle scanning dosage calculation sub-unit 802 is adapted to calculate high scanning dosages used for scanning one target position from different scanning angles based on equation $$N_i = \frac{N_j}{\sum_{i=1}^{V} \sqrt{A_{max,i}}} \ast \sqrt{A_{max,i}},$$

wherein $N_j$ is a scanning dosage on a $j^{th}$ target position, DoseRightFactor is an image noise coefficient, $N_{high}$ is the constant low scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

The scanning implementation sub-unit 803 is adapted to perform scanning based on the calculated scanning dosages on different target positions and the calculated scanning dosages used for scanning one target position from different scanning angles.

In some embodiments, when the scanning unit 602 uses the scanning dosage to scan the target position, the current in the tube filament is under open-loop control.

Figure 9:
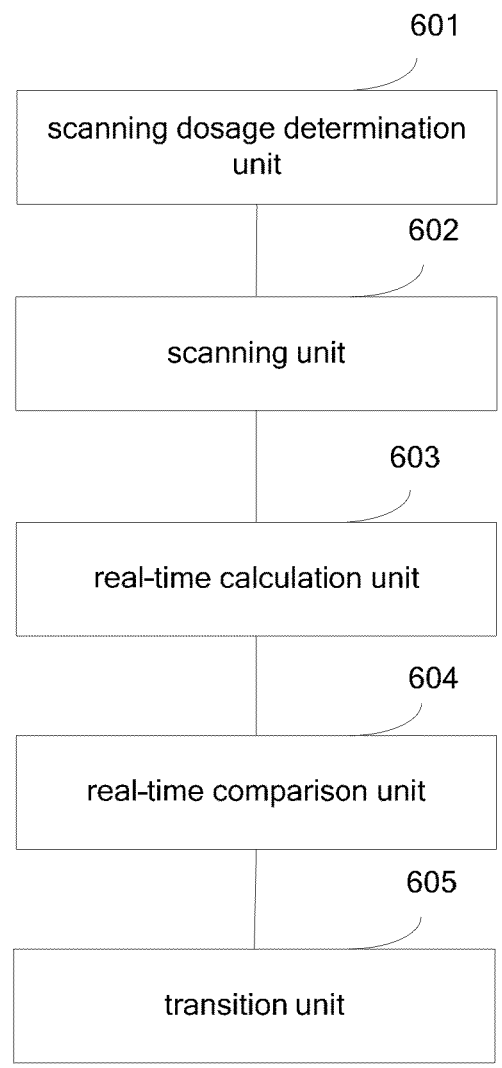
FIG. 9 schematically illustrates a block diagram of a scanning device according to one embodiment of the present disclosure.

In some embodiments, as shown in FIG. 9, the device may further include a real-time calculation unit 603, a real-time comparison unit 604 and a transition unit 605. The real-time calculation unit 603 is adapted to implement real-time calculation to obtain a time period for transmission from a current scanning dosage to an initial high scanning dosage in a next high scanning dosage stage during a transition process from a high scanning dosage stage to a low scanning dosage stage. The real-time comparison unit 604 is adapted to implement real-time comparison between the calculated time period and a preset time period. The transition unit 603 is adapted to terminate the transition process from the high scanning dosage stage to the low scanning dosage stage, terminate the low scanning dosage stage, and transit to the next high scanning dosage stage from a current time point, if the calculated time period is longer than or equal to the preset time period.

In some embodiments, the real-time calculation unit 603 may further include a fitting sub-unit, a ratio calculation sub-unit and an initial high scanning dosage calculation sub-unit. The fitting sub-unit is adapted to fit an equivalent diameter of the water phantom on a target position where the initial high scanning dosage is used based on equivalent diameters of the water phantom of a plurality of parts obtained in previous scannings. The ratio calculation sub-unit adapted to calculate a ratio of the equivalent diameter of water phantom on the target position where the initial high scanning dosage is used to an equivalent diameter of the water phantom on a target position where the current scanning dosage is used. The initial high scanning dosage calculation sub-unit, adapted to calculate a product of the ratio and the current scanning dosage as the initial high scanning dosage.

Compared with the conventional solutions, embodiments of the present disclosure have following advantages. An inconstant scanning dosage is determined according to two factors, including a trigger condition which varies regularly and attenuation fluctuations of an object to be scanned. The inconstant scanning dosage (including an inconstant high scanning dosage and an inconstant low scanning dosage) varies with a target position and a scanning angle on a same target position, so that the scanning dosage may have a relatively low value and image noise congruence may be ensured.

Further, a current high scanning dosage stage may be switched to a next high scanning dosage stage in a required time period, thereby avoiding delay of the next high scanning dosage stage.

Figure 10:
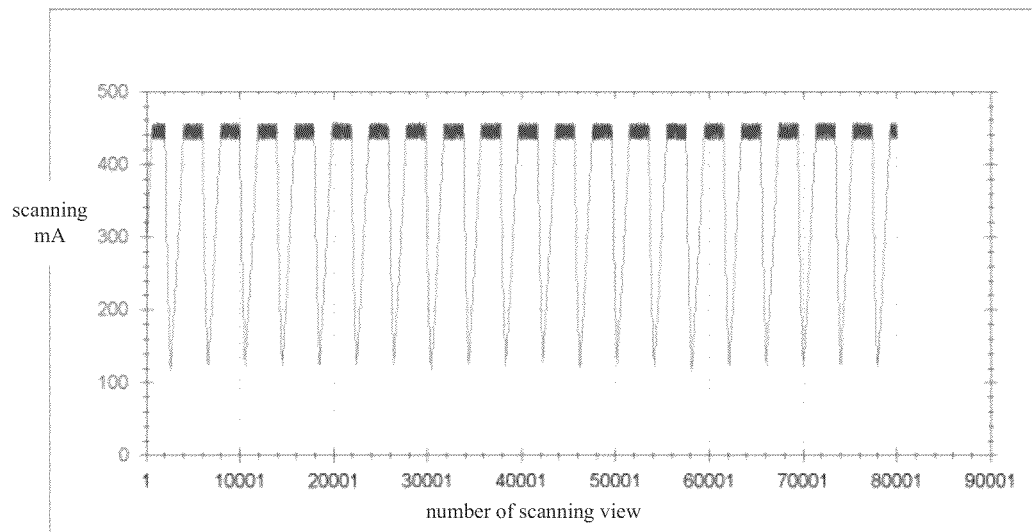
FIG. 10 schematically illustrates a heart scanning diagram based on variations of electrocardio signals in existing techniques.
Figure 11:
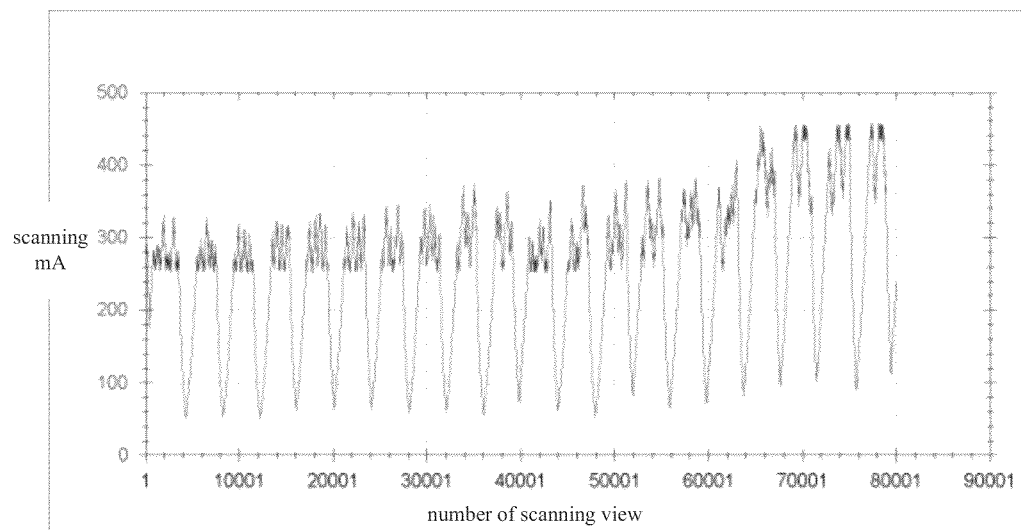
FIG. 11 schematically illustrates a heart scanning diagram after dosage adjustment according to one embodiment of the present disclosure.

The dosage adjustment method provided in the embodiments of the present disclosure may be applied in a heart scanning. A high dosage scanning region and a low dosage scanning region may be determined based on variations of electrocardio signals. And dosages in the high and low dosage scanning regions are calculated based on attenuation fluctuations of an object to be scanned. FIG. 10 schematically illustrates a heart scanning diagram based on variations of electrocardio signals in existing techniques and FIG. 11 schematically illustrates a heart scanning diagram after dosage adjustment according to one embodiment of the present disclosure. From FIGS. 10 and 11, in existing techniques, a high scanning dosage in the heart scanning remains at 450 and a low scanning dosage remains at 120. While in the embodiment of the present disclosure, a high scanning dosage varies within a range from about 260 to about 460 with attenuation fluctuations of a body to be scanned and a minimum low scanning dosage may be at 60. Therefore, image noise congruence is better and a scanning dosage is reduced in the present disclosure.

Those skilled in the art could understand that, working procedures of systems, devices and units described above may be referring to methods provided in embodiments above, which are not illustrated in detail here for brief.

It should be noted that systems, devices and methods provided in embodiments of the present disclosure are merely examples, which can be implemented in alternative ways. For example, system embodiments described above are only illustrative. Divisions of devices and units in the system are only examples for dividing logic functions. Other divisions may be employed in practice. For example, several units or components may be combined or integrated in another system, or some features can be ignored or not performed. Besides, couplings, direct couplings or communication connections between units may be realized by some interfaces. Indirect couplings or communication connections between devices or between units may be electrical, mechanical or of other forms.

Units described as separated components may be separated physically or not. Components illustrated as units may be physical units or not, that is, they may be disposed in a same place or distributed in a plurality of network cells. Some or all of the units may be selected according to practical requirements to implement embodiments of the present disclosure.

Besides, units in embodiments of the present disclosure may be integrated in one processing unit or be separated physically, or at least two units thereof are integrated in one processing unit. The integrated units may be implemented by hardware or software.

It should be noted that, those skilled in the art may understand all or some of the processes in the methods described above can be realized by using computer programs to instruct corresponding hardware. The programs may be stored in a readable storage medium in a computer. When the programs are implemented, the processes in the methods in the above embodiments may be performed. The readable storage medium may be diskette, CD (Compact Disc), ROM (Read-Only Memory), RAM (Random Access Memory) or the like.

A scanning method and device with a reduced scanning dosage are described. Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. A computed tomography (CT) scanning method, comprising:
    determining values for a first scanning dosage and a second scanning dosage used in a scanning process based on a trigger condition which varies regularly and attenuation fluctuations of an object to be scanned, wherein the first scanning dosage is higher than the second scanning dosage, and at least one of the first scanning dosage and the second scanning dosage has an inconstant value;
    scanning a target position with dosages at the determined values;
    during a transition process from the first scanning dosage stage to the second scanning dosage stage, implementing real-time calculation to obtain a time period for transition from a current scanning dosage to an initial scanning dosage in a third scanning dosage stage performed after the second scanning dosage stage;
    implementing real-time comparison between the calculated time period and a preset time period; and
    if the calculated time period is longer than or equal to the preset time period, terminating the transition process from the first scanning dosage stage to the second scanning dosage stage, terminating the second scanning dosage stage, and transitioning to the third scanning dosage stage from a current time point.

2. The method according to claim 1, wherein when the first scanning dosage has an inconstant value, the second scanning dosage has a constant value which is determined according to the trigger condition which varies regularly.

3. The method according to claim 1, wherein when the second scanning dosage has an inconstant value, the first scanning dosage has a constant value which is determined according to the trigger condition which varies regularly.

4. The method according to claim 1, wherein when the second scanning dosage has an inconstant value, the step of determining values for a first scanning dosage and a second scanning dosage used in a scanning process based on a trigger condition which varies regularly and attenuation fluctuations of an object to be scanned comprises:
- determining to use the inconstant second scanning dosage to scan the target position according to the trigger condition which varies regularly; and
- adjusting the second scanning dosage to be a dosage which varies with the target position or varies with the target position and a scanning angle based on a dosage adjustment mode to ensure image noise congruence.

5. The method according to claim 1, wherein when the first scanning dosage has an inconstant value, the step of determining values for a first scanning dosage and a second scanning dosage used in a scanning process based on a trigger condition which varies regularly and attenuation fluctuations of an object to be scanned comprises:
- determining to use the inconstant first scanning dosage to scan the target position according to the trigger condition which varies regularly; and
- adjusting the first scanning dosage to be a dosage which varies with the target position or varies with the target position and a scanning angle based on a dosage adjustment mode to ensure image noise congruence.

6. The method according to claim 4, wherein the step of adjusting the second scanning dosage to be a dosage which varies with the target position or varies with the target position and a scanning angle based on a dosage adjustment mode to ensure image noise congruence comprises:
- calculating a first set of dosage values for the second scanning dosage based on equation $$N_j = DoseRightFactor \times N_{low} \times \left( \frac{e^{(-\mu_{water} * D_{ref})}}{e^{(-\mu_{water} * D_j)}} \right)^{adjCoef},$$

wherein the first set of dosage values are used for scanning different target positions; and
calculating a second set of dosage values for the second scanning dosage based on equation $$N_i = \frac{N_j}{\sum_{i=1}^{V} \sqrt{A_{max,i}}} * \sqrt{A_{max,i}},$$

wherein the second set of dosage values are used for scanning one target position from different scanning angles,
wherein $N_j$ is a scanning dosage on a $j^{th}$ target position, DoseRightFactor is an image noise coefficient, $N_{low}$ is the second scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

7. The method according to claim 5, wherein the step of adjusting the first scanning dosage to be a dosage which varies with the target position or varies with the target position and a scanning angle based on a dosage adjustment mode to ensure image noise congruence comprises:
- calculating a first set of dosage values for the first scanning dosage based on equation $$N_j = DoseRightFactor \times N_{high} \times \left( \frac{e^{(-\mu_{water} * D_{ref})}}{e^{(-\mu_{water} * D_j)}} \right)^{adjCoef},$$

wherein the first set of dosage values are used for scanning different target positions; and
calculating a second set of dosage values for the first scanning dosage based on equation $$N_i = \frac{N_j}{\sum_{i=1}^{V} \sqrt{A_{max,i}}} * \sqrt{A_{max,i}},$$

wherein the second set of dosage values are used for scanning one target position from different scanning angles,
wherein $N_j$ is a scanning dosage on a $j^{th}$ target position, DoseRightFactor is an image noise coefficient, $N_{high}$ is the first scanning dosage, $\mu_{water}$ is an attenuation coefficient of water, $D_{ref}$ is a referenced equivalent diameter of the water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

8. The method according to claim 1, wherein when the target position is being scanned with the determined values, a current in a tube filament is under open-loop control.

9. The method according to claim 1, wherein the initial scanning dosage in the third scanning dosage stage is predicted by following steps:
- fitting an equivalent diameter of the water phantom on a target position where the initial scanning dosage is used based on equivalent diameters of the water phantom of a plurality of parts obtained in previous scannings;
- calculating a ratio of the equivalent diameter of water phantom on the target position where the initial scanning dosage is used to an equivalent diameter of the water phantom on a target position where the current scanning dosage is used; and
- calculating a product of the ratio and the current scanning dosage as the initial scanning dosage in the third scanning dosage stage.

10. A computed tomography (CT) scanning device, comprising:
- a scanning dosage determination unit, adapted to determine values for a first scanning dosage and a second scanning dosage used in a scanning process based on a trigger condition which varies regularly and attenuation fluctuations of an object to be scanned, wherein the first scanning dosage is higher than the second scanning dosage, and at least one of the first scanning dosage and the second scanning dosage has an inconstant value;
- a CT scanning unit, adapted to scan a target position with dosages at the determined values;
- a real-time calculation unit, adapted to implement real-time calculation to obtain a time period for transition from a current scanning dosage to an initial scanning dosage in a third scanning dosage stage performed after the second scanning dosage stage, during a transition process from the first scanning dosage stage to the second scanning dosage stage;

a real-time comparison unit, adapted to implement real-time comparison between the calculated time period and a preset time period; and a transition unit, adapted to terminate the transition process from the first scanning dosage stage to the second scanning dosage stage, terminate the second scanning dosage stage, and transition to the third scanning dosage stage from a current time point, if the calculated time period is longer than or equal to the preset time period.

11. The device according to claim 10, wherein when the first scanning dosage has an inconstant value, the second scanning dosage has a constant value which is determined according to the trigger condition which varies regularly.

12. The device according to claim 10, wherein when the second scanning dosage has an inconstant value, the first scanning dosage has a constant value which is determined according to the trigger condition which varies regularly.

13. The device according to claim 10, wherein when the second scanning dosage has an inconstant value, the scanning dosage determination unit comprises:
a first scanning mode determination sub-unit, adapted to determine to use the inconstant second scanning dosage to scan the target position according to the trigger condition which varies regularly; and
a first scanning dosage adjustment sub-unit, adapted to adjust the second scanning dosage to be a dosage which varies with the target position or varies with the target position and a scanning angle based on a dosage adjustment mode to ensure image noise congruence.

14. The device according to claim 10, wherein when the first scanning dosage has an inconstant value, the scanning dosage determination unit comprises:
a second scanning mode determination sub-unit, adapted to determine to use the inconstant first scanning dosage to scan the target position according to the trigger condition which varies regularly; and
a second scanning dosage adjustment sub-unit, adapted to adjust the first scanning dosage to be a dosage which varies with the target position or varies with the target position and a scanning angle based on a dosage adjustment mode to ensure image noise congruence.

15. The device according to claim 13, wherein the first scanning dosage adjustment sub-unit comprises:
a first position scanning dosage calculation sub-unit, adapted to calculate a first set of dosage values for the second scanning dosage based on equation $$N_j = DoseRightFactor \times N_{low} \times \left(\frac{e^{(-\mu_{water}*D_{ref})}}{e^{(-\mu_{water}*D_j)}}\right)^{adjCoef},$$

wherein the first set of dosage values are used for scanning different target positions; and
a first angle scanning dosage calculation sub-unit, adapted to calculate a second set of dosage values for the second scanning dosage based on equation $$N_i = \frac{N_j}{\sum_{i=1}^{V}\sqrt{A_{max,i}}} * \sqrt{A_{max,i}},$$

wherein the second set of dosage values are used for scanning one target position from different scanning angles, wherein $N_j$ is a scanning dosage on a $j^{th}$ target position, DoseRightFactor is an image noise coefficient, $N_{low}$ is the second scanning dosage, $\mu_{water}$ is an attenuation coefficient of water, $D_{ref}$ is a referenced equivalent diameter of a water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

16. The device according to claim 14, wherein the second scanning dosage adjusting sub-unit comprises:
a second position scanning dosage calculation sub-unit, adapted to calculate a first set of dosage values for the first scanning dosage based on equation $$N_j = DoseRightFactor \times N_{high} \times \left(\frac{e^{(-\mu_{water}*D_{ref})}}{e^{(-\mu_{water}*D_j)}}\right)^{adjCoef},$$

wherein the first set of dosage values are used for scanning different target positions; and
a second angle scanning dosage calculation sub-unit, adapted to calculate a second set of dosage values for the first scanning dosage based on equation $$N_i = \frac{N_j}{\sum_{i=1}^{V}\sqrt{A_{max,i}}} * \sqrt{A_{max,i}},$$

wherein the second set of dosage values are used for scanning one target position from different scanning angles,
wherein $N_j$ is a scanning dosage on a $j^{th}$ target position, DoseRightFactor is an image noise coefficient, $N_{high}$ is the first scanning dosage, $\mu_{water}$ is an attenuation coefficient of water, $D_{ref}$ is a referenced equivalent diameter of the water phantom, $D_j$ is an equivalent diameter of the water phantom on the $j^{th}$ target position, adjCoef is an exponent adjustment parameter of a current in a tube filament, $N_i$ is a scanning dosage of a $i^{th}$ scanning angle on the $j^{th}$ target position, $A_{max,i}$ is maximum attenuation of all channels of the $i^{th}$ scanning angle, and V is the total number of scanning angles in a round of scanning.

17. The device according to claim 10, wherein when the CT scanning unit scans the target position with the determined values, a current in a tube filament is under open-loop control.

18. The device according to claim 10, wherein the real-time calculation unit comprises:
a fitting sub-unit, adapted to fit an equivalent diameter of the water phantom on a target position where the initial scanning dosage is used based on equivalent diameters of the water phantom of a plurality of parts obtained in previous scannings;
a ratio calculation sub-unit, adapted to calculate a ratio of the equivalent diameter of water phantom on the target position where the initial scanning dosage is used to an equivalent diameter of the water phantom on a target position where the current scanning dosage is used; and
an initial scanning dosage calculation sub-unit, adapted to calculate a product of the ratio and the current scanning dosage as the initial scanning dosage in the third scanning dosage stage.

* * * * *